(12) United States Patent
Chida et al.

(10) Patent No.: US 8,981,283 B2
(45) Date of Patent: Mar. 17, 2015

(54) EVALUATION AID

(75) Inventors: Koichi Chida, Sendai (JP); Yuji Kaga, Yamagata (JP); Goro Yokouchi, Tokyo (JP)

(73) Assignees: National University Corporation, Tohoku University, Miyagi (JP); Mitaya Manufacturing Co., Ltd., Kawagoe-Shi Saitama (JP)

( * ) Notice: Subject to any disclaimer, the term of this patent is extended or adjusted under 35 U.S.C. 154(b) by 125 days.

(21) Appl. No.: 13/813,120

(22) PCT Filed: Jul. 26, 2011

(86) PCT No.: PCT/JP2011/066900
§ 371 (c)(1),
(2), (4) Date: Feb. 27, 2013

(87) PCT Pub. No.: WO2012/014862
PCT Pub. Date: Feb. 2, 2012

(65) Prior Publication Data
US 2013/0156164 A1    Jun. 20, 2013

(30) Foreign Application Priority Data
Jul. 30, 2010 (JP) .................. 2010-172570

(51) Int. Cl.
*G01D 18/00* (2006.01)
*A61B 6/00* (2006.01)

(52) U.S. Cl.
CPC . *A61B 6/58* (2013.01); *A61B 6/583* (2013.01); *A61B 6/585* (2013.01)

USPC .................................................. 250/252.1

(58) Field of Classification Search
CPC ......... A61B 8/587; G01R 33/58; G01T 7/005
USPC ...................................................... 250/252.1
See application file for complete search history.

(56) References Cited

U.S. PATENT DOCUMENTS 4,352,020 A * 9/1982 Horiba et al. .................. 378/18
5,841,835 A   11/1998 Aufrichtig et al.
6,409,383 B1   6/2002 Wang et al.
(Continued)

FOREIGN PATENT DOCUMENTS

JP   06-090941 A   4/1994
JP   11-004822 A   1/1999
(Continued)

OTHER PUBLICATIONS

Oda et al., "Establishment and standardization of a quality assurance program for computed radiography systems (report from the scientific research group)," Japanese Journal of Radiological Technology, vol. 59(1), 2003, pp. 97-116.
(Continued)

*Primary Examiner* — Kiho Kim
(74) *Attorney, Agent, or Firm* — Brinks Gilson & Lione

(57) ABSTRACT

An evaluation aid which can be used as a phantom (imitation lesion) when a digital X-ray image thereof is taken and then evaluation is carried out through the digital X-ray image. The evaluation aid is adapted to be used for taking a digital X-ray image thereof through which evaluation is carried out, and contains a substrate (plate-like body) including a plurality of regions having different X-ray absorption ratios and step members provided on the plate-like body.

8 Claims, 4 Drawing Sheets

(56) References Cited

U.S. PATENT DOCUMENTS

| | | | |
|---|---|---|---|
| 6,720,766 B2 * | 4/2004 | Parker et al. | 324/308 |
| 8,077,827 B2 * | 12/2011 | Perng | 378/56 |
| 2004/0227069 A1 | 11/2004 | Sendai et al. | |

FOREIGN PATENT DOCUMENTS

| | | | |
|---|---|---|---|
| JP | 2001-299736 A | 10/2001 |
| JP | 2002-291729 A | 10/2002 |
| JP | 2004-245623 A | 9/2004 |
| JP | 2004-298617 A | 10/2004 |

OTHER PUBLICATIONS

International Search Report for International Application No. PCT/JP2011/066900, dated Aug. 30, 2011, 2 pages.
Office Action, and English language translation thereof, in corresponding Japanese Application No. 2010-172570, dated Jul. 1, 2014, 6 pages.
Written Opinion of the International Searching Authority, and English language translation thereof, in corresponding International Application No. PCT/JP2011/066900, dated Aug. 30, 2011, 7 pages.
Office Action, and English translation thereof, in corresponding Chinese Application No. 201180033241.0, dated Sep. 3, 2014, 14 pages.

* cited by examiner

EVALUATION AID

This application is a 371 application of PCT/JP2011/066900 having an international filing date of Jul. 26, 2011, which claims priority to JP2010-172570 filed Jul. 30, 2010, the entire contents of which are incorporated herein by reference.

TECHNICAL FIELD

The present invention relates to an evaluation aid, and especially an evaluation aid adapted to be used for taking a digital X-ray image thereof through which evaluation is carried out.

RELATED ART

Quality control (QC) or quality assurance (QA) of a medical X-ray apparatus, or keeping an X-ray image quality in a required level is very important. Further, recent X-ray apparatuses have excellent performances, for example, X-ray apparatuses including flat panel detectors with wide dynamic ranges are in widespread use.

Such X-ray apparatuses having excellent performances are required to be checked in detail every day. Considering the fact that it is necessary to check the X-ray apparatus every day, it is preferred that a check operation thereof can be easily carried out. As an evaluation aid capable of easily carrying out such a check operation, there is known a digital image phantom proposed by Oda et al. (see Non-patent document 1).

By using the digital image phantom of Oda et al., spatial resolution or contrast resolution of a digital X-ray image can be evaluated.

Meanwhile, when roughly dividing a human body from the viewpoint of differences of X-ray absorption ratios, it can be classified into three parts including a high X-ray absorption part such as a bone, a middle X-ray absorption part such as an internal organ or a soft tissue and a low X-ray absorption part such as a lung (pneumatic organ).

However, in the case where the digital image phantom of Oda et al. is used, there is a problem in that an image quality of an X-ray image only for one X-ray absorption part can be evaluated, but image qualities of an X-ray image for X-ray absorption parts having different X-ray absorption ratios cannot be evaluated at once.

Further, the Ministry of Health, Labour and Welfare of Japan notified the ordinance defining safety control of medical equipment on Mar. 30, 2007. Therefore, importance of the quality control or the quality assurance of the X-ray apparatus is further increasing.

For these reasons, there is a demand for developing an evaluation aid (phantom) which can easily evaluate image qualities of an X-ray image for the X-ray absorption parts having different X-ray absorption ratios (detectability of imitation lesion) at once.

Non-patent document 1: Establishment and standardization of a quality assurance program for computed radiography systems (report from the scientific research group) Japanese Journal of Radiological Technology 59(1), 97-116, 2003

SUMMARY OF THE INVENTION

Problem to be Solved by the Invention

It is an object of the present invention to provide an evaluation aid which can be used as a phantom (imitation lesion) when a digital X-ray image thereof is taken and then evaluation is carried out through the digital X-ray image, and especially an evaluation aid which can be used for easily evaluating image qualities of a digital X-ray image for X-ray absorption parts having different X-ray absorption ratios at once.

Means for Solving Problem

In order to achieve the object, the present invention includes the following features (1) to (16).

(1) An evaluation aid adapted to be used for taking a digital X-ray image thereof, wherein evaluation is carried out through the digital X-ray image, the evaluation aid comprising:
  a plate-like body including a plurality of regions having different X-ray absorption ratios; and
  block-like bodies provided on the plate-like body so as to correspond to the plurality of regions, respectively, each block-like body including a plurality of subregions having different X-ray absorption ratios.

(2) The evaluation aid according to the above feature (1), wherein thicknesses and/or constituent materials of the plurality of regions of the plate-like body are different from each other, so that these regions have the different X-ray absorption ratios.

(3) The evaluation aid according to the above feature (1) or (2), wherein the plate-like body is formed by laminating plates having different planar sizes together, and
  wherein thicknesses of the plurality of regions of the plate-like body are different from each other due to differences of the number of the plates contained therein, so that these regions have the different X-ray absorption ratios.

(4) The evaluation aid according to the above feature (3), wherein planar shapes of the plurality of plates are different from each other.

(5) The evaluation aid according to any one of the above features (1) to (4), wherein the plate-like body is formed of a material containing copper as a major component thereof.

(6) The evaluation aid according to any one of the above features (1) to (5), wherein thicknesses and/or constituent materials of the plurality of subregions of each block-like body are different from each other, so that these subregions have the different X-ray absorption ratios.

(7) The evaluation aid according to any one of the above features (1) to (6), wherein a constituent material of each block-like body is different from a constituent material of the plate-like body.

(8) The evaluation aid according to the above feature (7), wherein an X-ray absorption ratio of the constituent material of each block-like body is lower than an X-ray absorption ratio of the constituent material of the plate-like body.

(9) The evaluation aid according to any one of the above features (1) to (8), wherein each block-like body is formed of a material containing aluminum, polymethyl methacrylate, polystyrene, polypropylene, carbon, or two or more of them as a major component thereof.

(10) The evaluation aid according to any one of the above features (1) to (9), further comprising wire assemblies provided on the plate-like body so as to correspond to the plurality of regions, respectively, each wire assembly including a plurality of wire rods arraigned at substantially even intervals.

(11) The evaluation aid according to the above feature (10), wherein cross sectional areas of the plurality of wire rods included in each wire assembly are different from each other.

(12) The evaluation aid according to the above feature (10) or (11), wherein a planar shape of the plate-like body is a quadrangular shape, and each wire assembly is provided so that the plurality of wire rods included therein are inclined with respect to one side of the plate-like body.

(13) The evaluation aid according to any one of the above features (10) to (12), wherein each wire rod is formed of a material containing iron, carbon, silicon, manganese, or two or more of them as a major component thereof.

(14) The evaluation aid according to any one of the above features (10) to (13), wherein each wire assembly is formed by firmly fixing the plurality of wire rods to a sheet material.

(15) The evaluation aid according to the above feature (14), wherein an X-ray absorption ratio of a constituent material of the sheet material is lower than X-ray absorption ratios of constituent materials of the plate-like body and each wire rod.

(16) The evaluation aid according to the above feature (14) or (15), wherein the sheet material is formed from a paper fibrous base material into which epoxy resin is impregnated.

Effects of the Invention

According to the present invention, image qualities of an X-ray image for a plurality of X-ray absorption parts having different X-ray absorption ratios can be easily and reliably evaluated at once.

DETAILED DESCRIPTION OF THE PREFERRED EMBODIMENTS

Hereinafter, detailed description will be made on an evaluation aid of the present invention based on a preferred embodiment described in the accompanying drawings.

Figure 1:
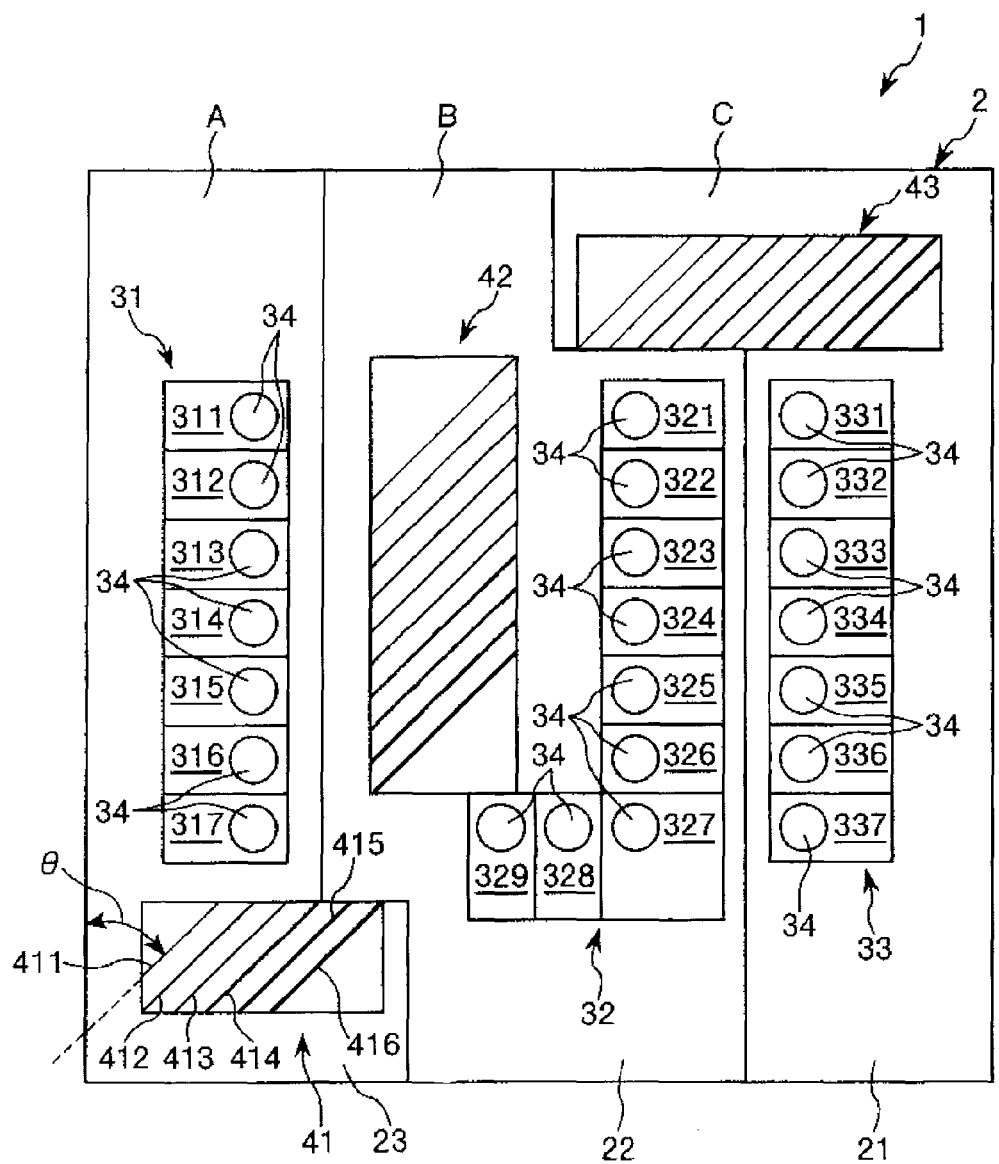
FIG. 1 is a plan view showing an embodiment of an evaluation aid of the present invention.
Figure 3:
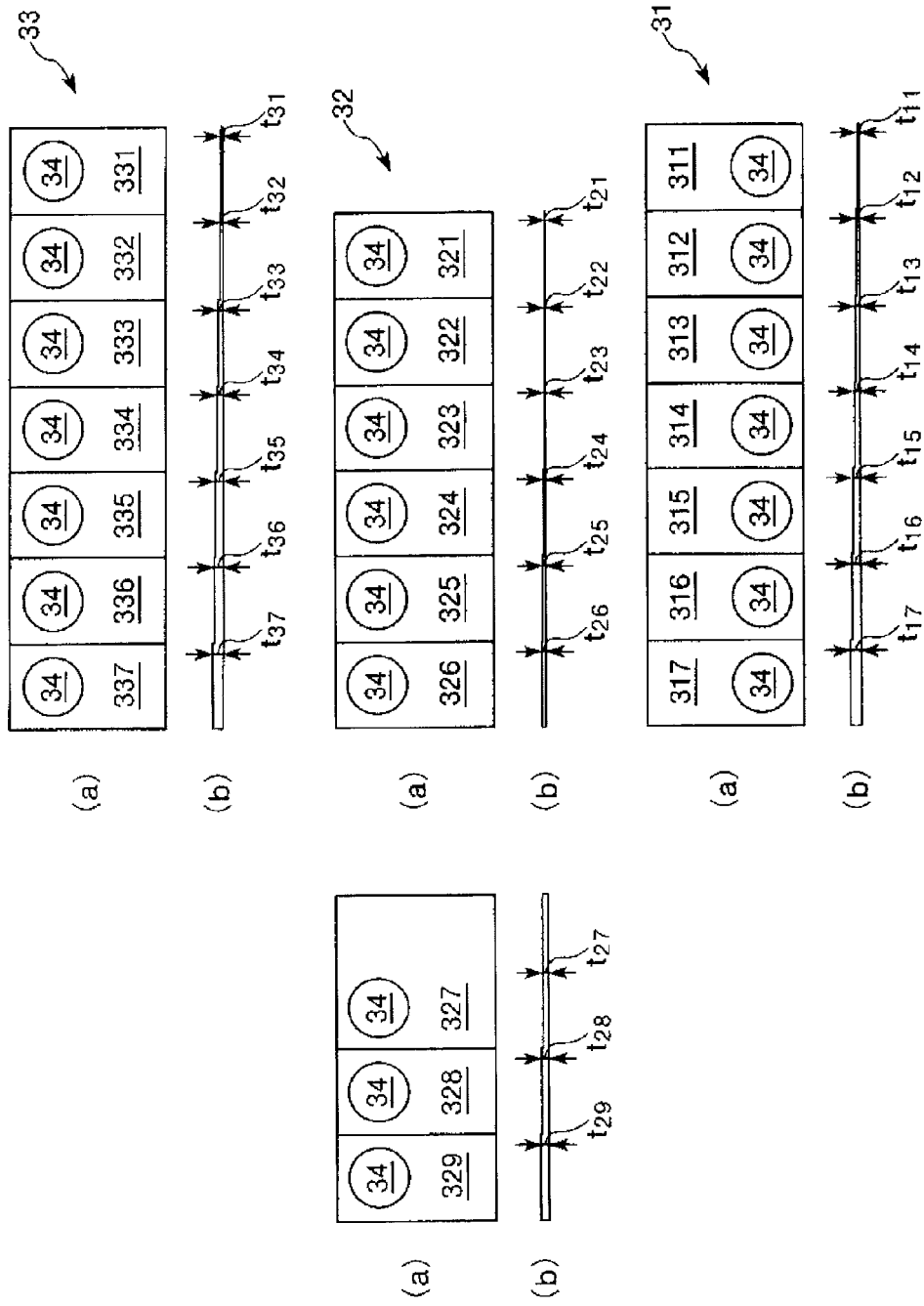
FIG. 3(a) is a plan view showing a structure of each block-like body provided on the plate-like body of the evaluation aid shown in FIG. 1.
FIG. 3(b) is a side view showing the structure of each block-like body of the evaluation aid shown in FIG. 1.
Figure 4:
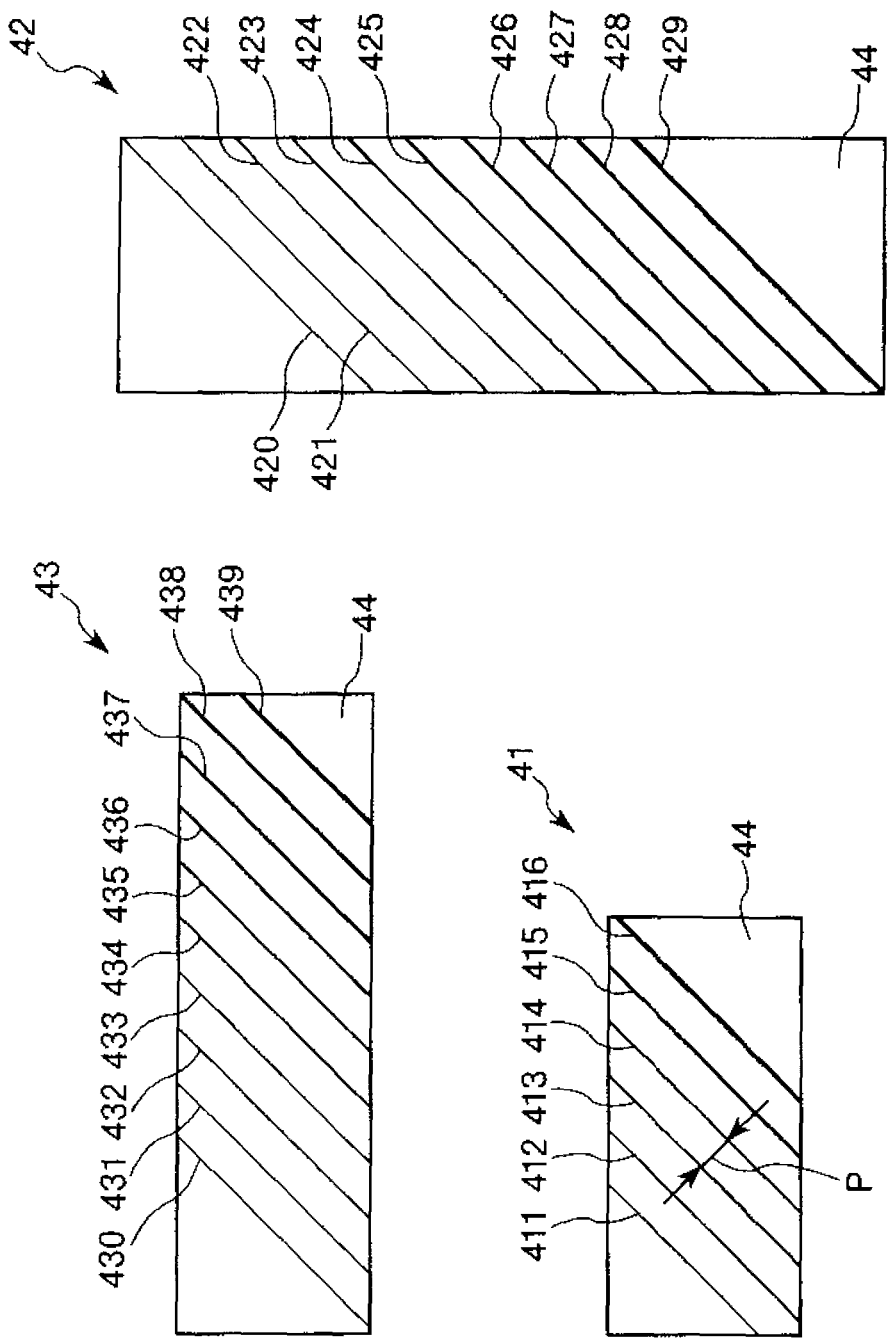
FIG. 4 is a plan view showing a structure of each wire assembly provided on the plate-like body of the evaluation aid shown in FIG. 1.

FIG. 1 is a plan view showing an embodiment of an evaluation aid of the present invention, FIG. 2(a) is a plan view showing a structure of the evaluation aid shown in FIG. 1, in which three plates of a plate-like body are shown in a disassembled manner for the purpose of clarity, FIG. 2(b) is a side view showing the structure of the plate-like body of the evaluation aid shown in FIG. 1, FIG. 3(a) is a plan view showing a structure of each block-like body provided on the plate-like body of the evaluation aid shown in FIG. 1, FIG. 3(b) is a side view showing the structure of each block-like body of the evaluation aid shown in FIG. 1, and FIG. 4 is a plan view showing a structure of each wire assembly provided on the plate-like body of the evaluation aid shown in FIG. 1.

An evaluation aid (phantom) 1 shown in FIG. 1 is used for taking a digital X-ray image (hereinafter, simply referred to as "X-ray image") thereof through which evaluation is carried out when conditions of an X-ray apparatus used for taking the X-ray image are to be checked.

After placing the evaluation aid 1 on the X-ray apparatus, an X-ray image of the evaluation aid 1 is taken by the X-ray apparatus. If the X-ray image does not have required image qualities, a condition of the X-ray apparatus is determined to be unusual and therefore it can be appropriately adjusted. This makes it possible for the X-ray apparatus to constantly provide an X-ray image having required image qualities (resolution). Therefore, it is possible to reliably prevent occurrence of medical accidents by poor X-ray images. As a result, it becomes possible to diagnose and treat diseases accurately.

The evaluation aid 1 has a substrate (plate-like body) 2, and a plurality of step members (block-like bodies) 31 to 33 and a plurality of wire charts (wire assemblies) 41 to 43 provided on the substrate 2, respectively.

Figure 2:
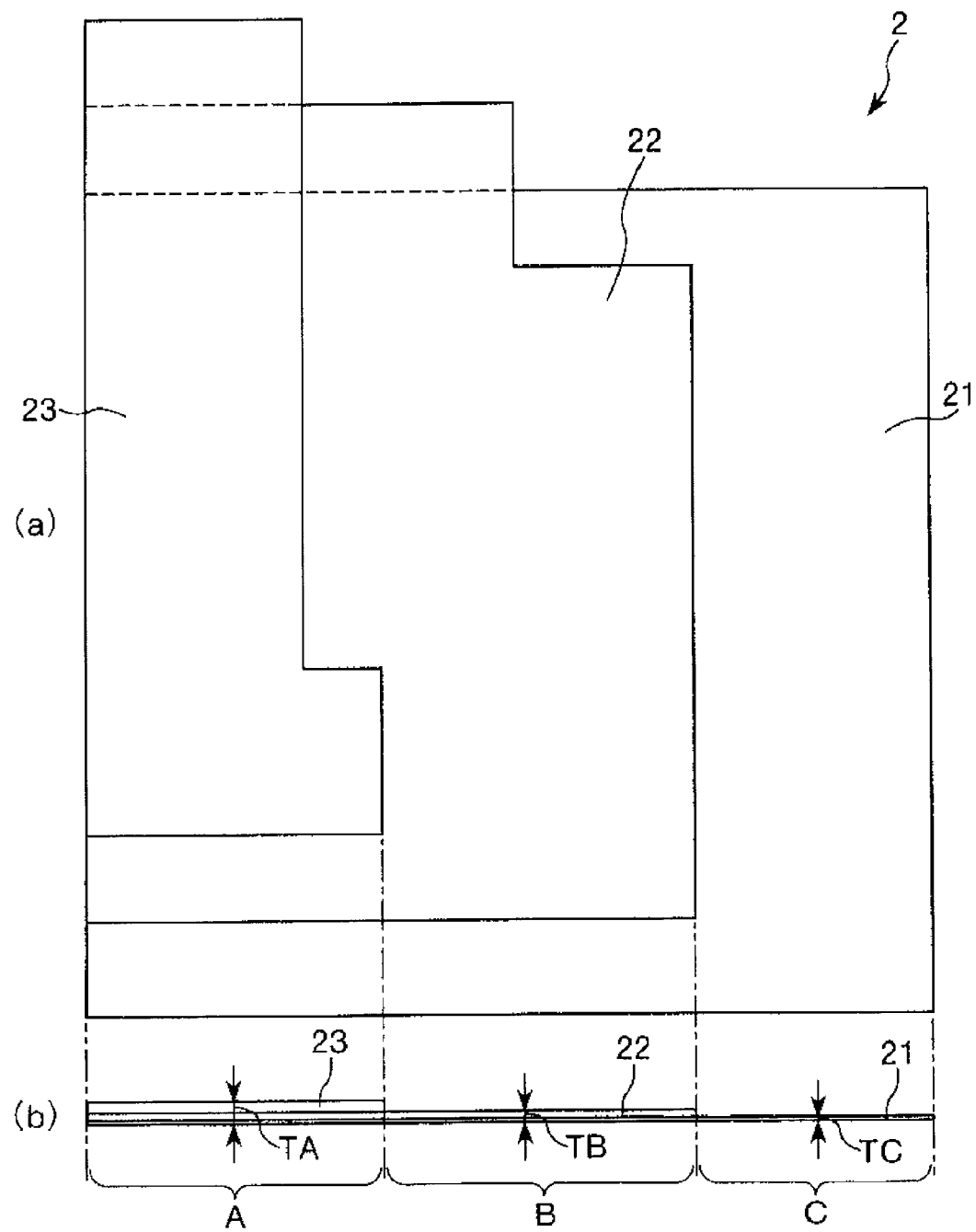
FIG. 2(a) is a plan view showing a structure of the evaluation aid shown in FIG. 1, in which three plates of a plate-like body are shown in a disassembled manner for the purpose of clarity.
FIG. 2(b) is a side view showing the structure of the plate-like body of the evaluation aid shown in FIG. 1.

An entire planar shape of the substrate 2 is a quadrangular shape (in this embodiment, a substantially square shape). As shown in FIGS. 1 and 2, this substrate 2 is formed by laminating a plurality of (in this embodiment, three) plates 21 to 23 together. In this regard, in FIG. 2(a), these three plates 21 to 23 are shown in a disassembled manner for the purpose of clarity.

Further, planar sizes of the plates 21 to 23 are different from each other. According to such a structure, the substrate 2 includes a region A formed by overlapping three plates 21 to 23, a region B formed by overlapping two plates 21 and 22, and a region C formed by one plate 21. Therefore, as shown in FIG. 2(b), thicknesses of the regions A to C are different from each other due to differences of the number of the plates 21 to 23 contained therein. As a result, the region A has the thickness of "TA", the region B has the thickness of "TB" and the region C has the thickness of "TC", respectively.

In this embodiment, the plates 21 to 23 are formed of the same material. As a result, the regions A to C have different X-ray absorption ratios, respectively. The region A has a maximum X-ray absorption ratio by setting the thickness "TA" thereof to a maximum value, the region C has a minimum X-ray absorption ratio by setting the thickness "TC" thereof to a minimum value, and the region B has a medium X-ray absorption ratio between the X-ray absorption ratio of the region A and the X-ray absorption ratio of the region C by setting the thickness "TB" thereof to a value between the thickness "TA" of the region A and the thickness "TC" of the region C, respectively.

According to such a structure, the region A can be considered to be a high X-ray absorption part of a human body such as a bone, the region B can be considered to be a middle X-ray absorption part such as an internal organ or a soft tissue, and the region C can be considered to be a low X-ray absorption part such as a lung (pneumatic organ), respectively. Therefore, by using such an evaluation aid 1, image qualities of an X-ray image for three X-ray absorption parts including the high X-ray absorption part, the middle X-ray absorption part and the low X-ray absorption part can be evaluated at once, and thus this is advantageous.

Further, it is preferred that the substrate 2 (that is, the plates 21 to 23) is constituted from a material having a relatively high X-ray absorption ratio, e.g., a material containing copper, tungsten, lead, titanium, iron, stainless steel, tin or the like as a major component thereof. Among them, it is preferred that the substrate 2 is constituted from the material containing copper as the major component thereof. This is because copper is comparatively inexpensive and has good workability and excellent safeness for living body.

The thicknesses of the regions A to C are not limited to specific values as long as they are set so that the regions A to C have different predetermined X-ray absorption ratios. In the case where the substrate 2 is constituted from copper, the thicknesses of the regions A to C are preferably set to the following values, respectively. Namely, the thickness "TA" of the region A is preferably in the range of about 0.5 to 7 mm, and more preferably in the range of about 1 to 5 mm. The thickness "TB" of the region B is preferably in the range of about 0.1 to 5 mm, and more preferably in the range of about 0.5 to 3 mm. The thickness "TC" of the region C is preferably in the range of about 0.05 to 3 mm, and more preferably in the range of about 0.1 to 2 mm.

In this embodiment, the X-ray absorption ratios of the regions A to C are set to the different values by changing the thickness of the substrate 2 (that is, the thickness of the regions A to C). However, the X-ray absorption ratios of the regions A to C may be set to the different values by changing the constituent materials thereof, or by changing the thicknesses thereof as well as the constituent materials thereof. In this regard, in the case where the X-ray absorption ratios of the regions A to C are set to the different values by changing the constituent materials thereof, an entire thickness of the substrate 2 may be set to a constant value. This makes it possible to obtain an evaluation aid 1 having a thinner thickness.

Further, planar shapes of the plurality of plates 21 to 23 are different from each other. Specifically, as shown in FIG. 2(a), the planar shape of the plate 21 is a square shape so as to correspond to an outer shape of the substrate 2, the planar shape of the plate 22 is such a shape that a part of a rectangle shape is cut, and the planar shape of the plate 23 is a roughly L-like shape, respectively. This makes it possible to properly arrange the step members 31 to 33 and the wire charts 41 to 43 on the substrate 2, while preventing these members (that is, the step members 31 to 33 and the wire charts 41 to 43) from spatially interfering with each other.

Since these members are properly arranged in the evaluation aid 1, there is an effect that occurrence of artifact, which would be generated due to diffuse reflection of X-ray at each of the members, can be suitably prevented when taking an X-ray image of the evaluation aid 1. Further, according to such an arrangement, there is also an effect that a rough positional relationship between parts having different X-ray absorption ratios (a mediastina thoracic vertebra part, a heart part and a lung-field part) in an actual chest front of a human body can be schematically shown.

A planar size of the plate 21 is preferably set to a value depending on a size of a detector of the X-ray apparatus, for example, to a value of about 200 mm×200 mm.

On such a substrate (plate-like body) 2, the step member (block-like body) 31 is provided in the region A, the step member 32 is provided in the region B, and the step member 33 is provided in the region C, respectively. Each of the step members 31 to 33 is firmly fixed to the substrate 2 using a method such as a welding method, a fusing method or a bonding method using an adhesive agent.

Each of the step members 31 to 33 is mainly used for evaluating contrast resolution of the obtained X-ray image for each of the regions A to C having different X-ray absorption ratios. In this regard, since these step members 31 to 33 have roughly the same structure, hereinafter the step member 31 will be representatively described.

The step member 31 is formed from one plate material having a planar shape being a rectangle shape and a side shape being a stepped shape (see FIG. 3). According to such a structure, the step member 31 includes a plurality of subregions 311 to 317 arranged along a longitudinal direction thereof and having different X-ray absorption ratios.

In this embodiment, a thickness "t1" of the subregion 311 is minimum, thicknesses of the subregions 312 to 317 increase from the subregion 312 toward the subregion 317, and a thickness "t17" of the subregion 317 is maximum. Due to these different thicknesses, the X-ray absorption ratio of the subregion 311 is minimum, the X-ray absorption ratios of the subregions 312 to 317 gradually increase from the subregion 312 toward the subregion 317, and the X-ray absorption ratio of the subregion 317 is maximum.

Therefore, in the case where the evaluation aid 1 is irradiated with X-ray having relatively high intensity, the X-ray is likely to pass through all subregions 311 to 317 so that the step member 31 is not clearly observed in the obtained X-ray image. With the decreased intensity of X-ray, the subregions 311 to 317 become gradually and clearly observed in the obtained X-ray image in the order of their high X-ray absorption ratios from the subregion 317.

For example, in the case where the subregion 315 is not clearly observed in an area of the X-ray image corresponding to the region A of the substrate 2 even if the evaluation aid 1 is irradiated with X-ray having such intensity that the subregions 315 to 317 are to be clearly observed, this means that the intensity of the X-ray is higher than a predetermined intensity thereof (or sensibility change of the detector of the X-ray apparatus occurs). In this way, it can be determined that adjustment of the X-ray apparatus is necessary.

The step member 32 includes subregions 321 to 329 having different X-ray absorption ratios, and the subregions 321 to 329 have different thicknesses of "t21" to "t29", respectively. The step member 33 includes subregions 331 to 337 having different X-ray absorption ratios, and the subregions 331 to 337 have different thicknesses of "t31" to "t37", respectively.

Further, seven through holes 34 are respectively formed through the step member 31 so as to correspond to the subregions 311 to 317. When the step member 31 is provided on the substrate 2, a surface of the substrate 2 is exposed from the step member 31 through holes 34. Therefore, within the region A, X-ray transmittance of a portion corresponding to each through hole 34 becomes equal to that of a surrounding portion of the step member 31, that is, X-ray transmittance of an area of the substrate 2 where the step member 31 is not provided. It becomes easy to confirm an imaging degree of the step member 31 (each of the subregions 311 to 317) in the X-ray image.

Further, a convex portion may be provided on each of the subregions 311 to 317 instead of the through hole 34. This makes it possible to differentiate X-ray absorption ratios between a portion where the convex portion is provided and other portion.

Further, it is preferred that a constituent material of the step member 31 is different from a constituent material of the substrate 2, and it is more preferred that an X-ray absorption ratio of the constituent material of the step member 31 is lower than an X-ray absorption ratio of the constituent material of the substrate 2. This makes it possible to prevent the step member 31 (32 or 33) itself from interfering with the evaluation of the contrast resolution of the X-ray image for the region A (B or C).

Concretely, it is preferred that the step member 31 is, for example, formed of aluminum, carbon or a material which will be exemplified below in connection with a sheet material 44. In particular, it is preferred that the step member 31 is formed of a material containing aluminum, polymethyl methacrylate, polystyrene, polypropylene, carbon, or two or more of them as a major component thereof.

This is because these materials have low X-ray absorption ratios, are relatively inexpensive, and have superior workability. In this regard, in the case where these materials are used in combination, the step member 31 may be formed of a mixture of the above materials, or may be formed by laminating base materials each formed of one of the above materials together.

The thicknesses "t11" to "t17" of the subregions 311 to 317 are not limited to specific values as long as they are set so that the subregions 311 to 317 have different predetermined X-ray absorption ratios. In the case where the step member 31 is formed of aluminum, the thickness of each of the subregions 311 to 317 is set to a value falling preferably within the range of about 0.01 to 5 mm, and more preferably within the range of 0.5 to 3.5 mm.

Further, a thickness difference between the adjacent subregions 311 to 317 (that is, a difference in height between the adjacent subregions 311 to 317) is not limited to a specific value, but is preferably in the range of about 0.05 to 2 mm, and more preferably in the range of 0.1 to 1 mm.

In this embodiment, the X-ray absorption ratios of the subregions 311 to 317 are set to the different values by changing the thickness of the step member 31 (that is, the thicknesses of the subregions 311 to 317). However, the X-ray absorption ratios of the subregions 311 to 317 may be set to the different values by changing the constituent materials thereof, or by changing the thicknesses thereof as well as the constituent materials thereof.

Such step members 31 to 33 can be formed by, for example, pressing plate materials.

Further, on such a substrate (plate-like body) 2, a wire chart (wire assembly) 41 is provided in the region A, a wire chart 42 is provided in the region B, and a wire chart 43 is provided in the region C, respectively. Each of the wire charts 41 to 43 is firmly fixed to the substrate 2 using a method such as a welding method, a fusing method or a bonding method using an adhesive agent.

Each of the wire charts 41 to 43 is mainly used for evaluating spatial resolution of the obtained X-ray image for each of the regions A to C having different X-ray absorption ratios. In this regard, since these wire charts 41 to 43 have roughly the same structure, hereinafter the wire chart 41 will be representatively described.

The wire chart 41 includes a plurality of wires (wire rods) 411 to 416 arraigned at substantially even intervals, and two sheet materials 44 between which each of the wires 411 to 416 is firmly fixed by being sandwiched.

Each of the wires 411 to 416 is formed from a wire rod having a circular cross section. These wires 411 to 416 have different diameters (cross sectional areas), respectively. In this way, by arranging the plurality of wires 411 to 416 having different sizes, it becomes possible to evaluate spatial resolution of the obtained X-ray image easily, wherein the term "spatial resolution" means which of these wires having different diameters can be visually observed in the obtained X-ray image. In this embodiment, as shown in FIG. 4, the diameter becomes large from the wire 411 toward the wire 416.

The diameter of each of the wires 411 to 416 is preferably set to a value falling within the range of about 0.01 to 3 mm, and more preferably within the range of about 0.05 to 1.5 mm.

Further, a distance (pitch) "P" between the wires 411 to 416 is preferably in the range of about 1 to 10 mm, and more preferably in the range of about 3 to 7 mm.

A cross sectional shape of each of the wires 411 to 416 is not limited to a circular shape, but may be an ellipsoidal shape, a quadrangular shape such as a rectangle shape or a square shape, or a polygonal shape such as a triangular shape, a pentagonal shape or a hexagonal shape.

Each of such wires 411 to 416 is arranged so as to be inclined with respect to one side (for example, a left side in FIG. 1) of the substrate 2. In this way, by arranging each of the wires 411 to 416 so as to be inclined with respect to the one side of the substrate 2, it is possible to prevent occurrence of artifact.

Specifically, if each of the wires 411 to 416 is arranged so as not to be inclined with respect to the one side of the substrate 2, but be parallel or vertical thereto, there is a case that each of the wires 411 to 416 interferes with a detecting system of the X-ray apparatus such as pixels (picture elements) of a digital X-ray image or X-ray grids. In this case, there is a possibility that moires, that is, interference fringes are generated in the obtained X-ray image.

On the other hand, by arranging each of the wires 411 to 416 so as to be inclined with respect to the one side of the substrate 2, it is possible to prevent or suppress the above problem.

An inclination angle "θ" of each of the wires 411 to 416 is not limited to a specific value, but is preferably in the range of about 30 to 75°, and more preferably in the range of about 40 to 55°. This makes it possible to more preferably prevent the occurrence of the artifact.

For example, each of the wires 411 to 416 can be used by cutting a piano wire, a guide wire or the like. It is preferred that each of the wires 411 to 416 is formed of a material containing iron, carbon, silicon, manganese, or two or more of them (e.g., alloy) as a major component thereof. This makes it possible to more reliably evaluate the spatial resolution of the X-ray image for each of the regions A to C having different X-ray absorption ratios.

Each of the wires 411 to 416 is firmly fixed between the two sheet materials 44 by bonding them using a method such as a welding method, a fusing method or a bonding method using an adhesive agent.

The wire chart 42 is formed by sandwiching a plurality of wires 420 to 429 between two sheet materials 44, and the wire chart 43 is formed by sandwiching a plurality of wires 430 to 439 between two sheet materials 44.

Further, a constituent material of the sheet material 44 is not limited to a specific kind, but it is preferred that an X-ray absorption ratio thereof is lower than the X-ray absorption ratios of the constituent materials of the substrate 2 and each of the wires 411 to 416. This makes it possible to prevent the wire chart 41 (42 or 43) itself from interfering with the evaluation of the contrast resolution of the X-ray image for the region A (B or C).

Examples of the sheet material 44 include a base material made of a synthetic resin, a fibrous base material, a fibrous base material into which a synthetic resin is impregnated, and the like. In this regard, examples of the synthetic resin include various kinds of thermoplastic resins such as polyolefin (e.g., polyethylene or polypropylene), polyamide, polyester, polyphenylene sulfide, polycarbonate, polymethyl methacrylate and polyether; various kinds of thermosetting resins such as epoxy resin, and acrylic resin; various kinds of thermoplastic elastomers; and the like. Further, examples of the fibrous base material include a paper fibrous base material, a carbon fibrous base material, a glass fibrous base material and the like.

Among them, it is preferred that the sheet material 44 is formed from a paper fibrous base material into which the epoxy resin is impregnated (paper epoxy sheet). Use of the paper fibrous base material into which the epoxy resin is impregnated makes it possible to prevent an X-ray absorption ratio of the wire chart 41 from increasing. Further, the paper fibrous base material into which the epoxy resin is impregnated has advantages in that it can be easily processed as compared to another base material and can be manufactured at a low cost.

These wire charts 41 to 43 may be formed by bonding the plurality of wires 411 to 416, the plurality of wires 420 to 429 and the plurality of wires 430 to 439 together using an adhesive agent or the like. Further, the plurality of wires 411 to 416, the plurality of wires 420 to 429 and the plurality of wires 430 to 439 may be directly secured onto the substrate 2.

For example, evaluation is carried out through an X-ray image of such an evaluation aid 1, as follows.

First, the evaluation aid 1 is placed on an X-ray apparatus at a side of a detector thereof, and then X-ray is emitted from an X-ray emitter of the X-ray apparatus to the detector thereof to thereby take an X-ray image of the evaluation aid 1.

Next, within areas of the obtained X-ray image corresponding to the regions A to C of the evaluation aid 1, it is checked (evaluated) whether or not predetermined subregions of the steps 31 to 33 can be visually observed. Further, it is also checked (evaluated) whether or not predetermined wires of the wire charts 41 to 43 can be clearly observed.

At this time, in the case where an X-ray image having required contrast resolution and spatial resolution is obtained, it can be determined that a condition of the X-ray apparatus is normal. On the other hand, in the case where image qualities of an X-ray image for some areas are blurred or smudgy, that is, an X-ray image that does not have required contrast resolution and/or spatial resolution is obtained, it is determined that the condition of the X-ray apparatus is unusual, and therefore it can be adjusted so as to obtain an X-ray image having predetermined image qualities.

As described above, according to the present invention, it is possible to accurately and reliably evaluate contrast resolution and/or spatial resolution of an X-ray image for a plurality of X-ray absorption parts having different X-ray absorption ratios at once, while preventing contrast between areas of the X-ray image from decreasing.

Namely, it is possible to easily evaluate image qualities of an X-ray image for three parts including a high X-ray absorption part of a human body such as a bone, a middle X-ray absorption part such as an internal organ or a soft tissue and a low X-ray absorption part such as a lung (pneumatic organ) in a state of simulating (reflecting) real clinical use. This makes it possible to more clinically and practically evaluate the image qualities of the obtained X-ray image.

Therefore, it is possible to reliably prevent occurrence of medical accidents by poor X-ray images. As a result, it becomes possible to diagnose and treat diseases accurately.

On the other hand, in the case where three conventional phantoms respectively capable of evaluating image qualities of X-ray images for the three X-ray absorption parts are used at the same time for an X-ray apparatus, the X-ray apparatus automatically corrects contrast of an obtained X-ray image (resultant X-ray image) based on a dose of X-ray passing through the phantom for the high X-ray absorption part.

Therefore, there is a problem in that the image qualities of the obtained X-ray image cannot be reliably evaluated due to decrease of contrast of the entire X-ray image. Namely, it is impossible to clinically and practically evaluate the image qualities of the obtained X-ray image.

While the evaluation aid of the present invention has been described based on the embodiment shown in the drawings hereinabove, the present invention shall not be limited thereto. Each structure constituting the evaluation aid may be substituted with an arbitrary structure having the same function as it. Further, arbitrary structures also may be added thereto.

For example, in the above embodiment, the substrate 2 includes three regions having different X-ray absorption ratios, but may include two regions or four or more regions depending on purpose thereof.

Industrial Applicability

According to the evaluation aid of the present invention, it is possible to evaluate image qualities of an X-ray image for X-ray absorption parts having different X-ray absorption ratios at once. Therefore, the present invention provides industrial applicability.

The invention claimed is:

1. An evaluation aid adapted to be used for taking a digital X-ray image thereof, wherein evaluation is carried out through the digital X-ray image, the evaluation aid comprising:
   a plate-like body being formed by laminating plates having different planar sizes together, the plate-like body including a plurality of regions having different X-ray absorption ratios, the different X-ray absorption ratios being obtained by at least different thickness of the plurality of regions due to differences of the number of the plates contained therein; and
   block-like bodies provided on the plate-like body so as to correspond to the plurality of regions, respectively, each block-like body including a plurality of subregions having different X-ray absorption ratios.

2. The evaluation aid as claimed in claim 1, wherein the different X-ray absorption ratios are obtained by further different constituent materials of the plurality of regions of the plate-like body.

3. The evaluation aid as claimed in claim 1, wherein thicknesses and/or constituent materials of the plurality of subregions of each block-like body are different from each other, so that these subregions have the different X-ray absorption ratios.

4. The evaluation aid as claimed in claim 1, wherein a constituent material of each block-like body is different from a constituent material of the plate-like body.

5. The evaluation aid as claimed in claim 4, wherein an X-ray absorption ratio of the constituent material of each block-like body is lower than an X-ray absorption ratio of the constituent material of the plate-like body.

6. An evaluation aid adapted to be used for taking a digital X-ray image thereof, wherein evaluation is carried out through the digital X-ray image, the evaluation aid comprising:
   a plate-like body including a plurality of regions having different X-ray absorption ratios;
   block-like bodies provided on the plate-like body so as to correspond to the plurality of regions, respectively, each block-like body including a plurality of subregions having different X-ray absorption ratios; and
   wire assemblies provided on the plate-like body so as to correspond to the plurality of regions, respectively, each wire assembly including a plurality of wire rods arraigned at substantially even intervals.

7. The evaluation aid as claimed in claim 6, wherein a planar shape of the plate-like body is a quadrangular shape, and each wire assembly is provided so that the plurality of wire rods included therein are inclined with respect to one side of the plate-like body.

8. The evaluation aid as claimed in claim 6, wherein cross sectional areas of the plurality of wire rods included in each wire assembly are different from each other.

* * * * *

UNITED STATES PATENT AND TRADEMARK OFFICE
CERTIFICATE OF CORRECTION

PATENT NO. : 8,981,283 B2  
APPLICATION NO. : 13/813120  
DATED : March 17, 2015  
INVENTOR(S) : Koichi Chida et al.

It is certified that error appears in the above-identified patent and that said Letters Patent is hereby corrected as shown below:

On the Title Page

Left column, item (75), replace "Sendai" with --Miyagi--.

Left column, item (73), after "Manufacturing Co., Ltd..," replace "Kawagoe-Shi" with --Kawagoe-shi--.

Signed and Sealed this  
Twenty-fourth Day of November, 2015

Michelle K. Lee  
*Director of the United States Patent and Trademark Office*